United States Patent [19]

Eberhard et al.

[11] Patent Number: 5,463,666
[45] Date of Patent: Oct. 31, 1995

[54] HELICAL AND CIRCLE SCAN REGION OF INTEREST COMPUTERIZED TOMOGRAPHY

[75] Inventors: Jeffrey W. Eberhard; Kwok C. Tam, both of Schenectady, N.Y.

[73] Assignee: General Electric Company, Schenectady, N.Y.

[21] Appl. No.: 150,318

[22] Filed: Nov. 12, 1993

[51] Int. Cl.$^6$ .............................. A61B 6/03; G01N 23/08
[52] U.S. Cl. ..................... 378/4; 378/901; 364/413.15; 364/413.19
[58] Field of Search .................... 378/4, 15, 901; 364/413.13, 413.14, 413.15, 413.16, 413.19

[56] References Cited

U.S. PATENT DOCUMENTS

| | | | |
|---|---|---|---|
| 5,032,990 | 7/1991 | Eberhard et al. | 364/413.15 |
| 5,187,659 | 2/1993 | Eberhard et al. | 364/413.15 |
| 5,257,183 | 10/1993 | Tam | 364/413.19 |
| 5,278,884 | 1/1992 | Eberhard et al. | 378/4 |
| 5,319,693 | 12/1992 | Eberhard et al. | 378/19 |
| 5,365,560 | 11/1994 | Tam | 378/8 |
| 5,383,119 | 1/1995 | Tam | 364/413.19 |
| 5,390,111 | 2/1995 | Tam | 364/413.14 |
| 5,390,112 | 2/1995 | Tam | 364/413.15 |
| 5,390,226 | 2/1995 | Tam | 378/19 |

OTHER PUBLICATIONS

"Image Reconstruction from Cone–Beam Projections: Necessary and Sufficient Conditions and reconstruction Methods", B. D. Smith, IEEE Transactions Medical Imaging, MI–4 (1985), pp. 14–25.

"Three–Dimensional Helical Scan Computed Tomography Using Cone–Beam Projections", Kudo & Saito, Journal of Systems and Computers in Japan, vol. 23, No. 12, pp. 75–82 (1992)

"Cone–Beam Tomography: Recent Advances and a Tutorial Review", B. D. Smith, Optical Engineering, May 1990, vol. 29, No. 5, pp. 524–534.

*Primary Examiner*—David P. Porta
*Assistant Examiner*—David Vernon Bruce
*Attorney, Agent, or Firm*—Paul R. Webb, II

[57] ABSTRACT

Imaging of a region of interest within a larger object is accomplished without the need for determining Radon derivatives of portions of the object outside a field of view which generally corresponds to the region of interest. The field of view and region of interest may be relatively large compared to a relatively small area detector used for the imaging. In order to provide a complete data set satisfying Radon completeness requirements with little or no collection of data from outside the region of interest, a source scanning trajectory uses a first circle, a second circle, and a helical portion connecting the first and second circles. The first and second circle and helical portion define a cylinder which is outside and surrounding the field of view, which is likewise a cylinder.

21 Claims, 6 Drawing Sheets fig. 1 fig. 2 fig. 3 fig. 4 fig. 5 fig. 6

HELICAL AND CIRCLE SCAN REGION OF INTEREST COMPUTERIZED TOMOGRAPHY

CROSS REFERENCE TO RELATED APPLICATIONS

The invention disclosed and claimed herein is related to the subject matter of the following commonly-assigned patent applications, the entire disclosures of which are hereby incorporated by reference:

Ser. No. 07/631,818, filed Dec. 21, 1990, now abandoned, in the name of Kwok C. Tam, entitled "PARALLEL PROCESSING METHOD AND APPARATUS FOR RECONSTRUCTING A THREE-DIMENSIONAL COMPUTERIZED TOMOGRAPHY (CT) IMAGE OF AN OBJECT FROM CONE BEAM PROJECTION DATA OR FROM PLANAR INTEGRAL";

U.S. Pat. No. 5,257,183, issued Oct. 26, 1992, in the name of Kwok C. Tam, entitled "METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT";

Ser. No. 07/725,142, filed Jul. 3, 1991, now U.S. Pat. No. 5,383,119, in the name of Kwok C. Tam, entitled "IMAGING WITH IMPROVED CONVERSION OF CONE BEAM DATA TO RADON DATA";

Ser. No. 08/100,818, filed Aug. 2, 1993, in the name of Kwok C. Tam, entitled "TOMOGRAPHY WITH GENERATION OF RADON DATA ON POLAR GRID POINTS"; and Ser. No. 08/131,180, filed Oct. 4, 1993, now U.S. Pat. No. 5,390,112, in the name of Kwok C. Tam, entitled "THREE-DIMENSIONAL COMPUTERIZED TOMOGRAPHY SCANNING METHOD AND SYSTEM FOR IMAGING LARGE OBJECTS WITH SMALLER AREA DETECTORS".

BACKGROUND OF THE INVENTION

The present invention relates generally to imaging using cone beam scanning. More specifically, it relates to such three-dimensional (3D) tomographic imaging using a scan pattern to image a region of interest.

In conventional computerized tomography (CT) for both medical and industrial applications, an x-ray fan beam and a linear array detector are used. Two-dimensional (2D) imaging is achieved. While the data set may be complete and image quality is correspondingly high, only a single slice of an object is imaged at a time. When a 3D image is required, a stack of slices approach is employed. Acquiring a 3D data set on 2D slice at a time is inherently slow. Moreover, in medial applications, motion artifacts occur because adjacent slices are not imaged simultaneously. Also, dose utilization is less than optimal because the distance between slices is typically less than the x-ray collimator aperture, resulting in double exposure to many parts of the body. In 2D CT, the scanning path of the source is often a simply circular scan about the object. The linear array detector is fixed relative to the source. (Although it is usual to talk about a scan path of a source relative to the object to be imaged, it is to be appreciated that the object may be rotated or otherwise moved to provide relative motion between the object and the source.)

In a system employing true cone beam geometry for 3D imaging, a cone beam x-ray source and a 2D area detector are used. An object is scanned, preferably over a 360° angular range, either by moving the x-ray source in a scanning circle about the object or by rotating the object while the source remains stationary. In either case, the area detector is fixed relative to the source. The relative movement between the source and object which is to be imaged provides scanning in either case. Compared to the conventional 2D stack of slices approach to achieve 3D imaging, the cone beam geometry has the potential to achieve rapid 3D imaging of both medical and industrial objects with improved dose utilization.

In order to provide a complete set of projection data for accurate imaging of an object of interest or a region of interest in an object, it is necessary to satisfy completeness criteria. These criteria, which are described in detail in Smith, B. D., "Image Reconstruction from Cone-Beam Projections: Necessary and Sufficient Conditions and Reconstruction Methods", IEEE Transactions Medical Imaging, MI-4 (1985) pp. 14–25, hereby incorporated by reference, basically require that any plane passing through the object or region of interest must intersect the scan path at one or more locations.

The completeness criteria are also discussed in Ser. No. 07/725,142, incorporated by reference above and which discards unwanted Radon data while obtaining a complete data set.

The 3D CT imaging generally uses a Radon transform approach. (Radon transforms are also used in 2D CT.) The object is defined in terms of its x-ray attenuation coefficient. The measured cone beam projection data corresponds to a line integral of this function over the radial direction from the radiation source to a particular detector element within the detector array. The 3D Radon transform of an object at a point is given by the area integral of the x-ray attenuation coefficient over the plane passing through the point, which plane is perpendicular to the line from the origin to the particular point. If parallel beams of x-rays are applied to the object which is to be imaged, line integrals of the detector data are equal to the Radon transform of the object. However, obtaining the Radon transform is significantly more complex where a cone beam of x-ray or other imaging energy is applied to the object. In that case, obtaining the Radon transform, also called Radon data, is significantly more difficult. Once Radon data is obtained, an inverse Radon transformation is used to convert the Radon data into a reconstructed image which is then displayed.

The U.S. Pat. No. 5,257,183 incorporated by reference above, discloses a technique for calculating the radial derivative of Radon data from cone beam data. The incorporated by reference application Ser. No. 07/631,818 discloses a technique for inverting the Radon data to obtain the reconstructed image of the object which is being viewed. In order to perform the Radon inversion, Radon data (as opposed to derivatives of Radon data) is required (except where using those few techniques which perform Radon inversion using derivative data) and the Radon data should reside on polar grids on a number of predetermined vertical planes containing the Z axis as the common axis. These requirements arise because the first part of the Radon inversion process is a two dimensional (2D) CT image reconstruction on each vertical plane, which takes input data in the form of Radon data at equally spaced angle θ and equally spaced detector spacings s. However, the technique of the referenced U.S. Pat. No. 5,257,183 initially produces radial derivatives of the Radon data, instead of Radon data itself, and the derivative data is generated on a spherical shell having as its diameter a line segment so connecting a source position s and an origin o (instead of being generated on the points of the polar grids). The U.S. Pat. No. 5,257,183 further describes techniques for converting from the radial derivative of Radon data to Radon data itself and to obtain the Radon data on the polar grid points by use of the Radon data relative to the spherical shell, often called the Radon shell. However, the calculation of Radon data over the spherical Radon shell requires a relatively large amount of processing or computational power. Further, using that Radon data to provide Radon data at the points on the polar grid of the vertical planes requires relatively complex techniques which, in effect, involve interpolation of different data points on the Radon shell over the shell. This three-dimensional (3D) interpolation is relatively complex and accordingly requires large amounts of computational power.

The previous application Ser. No. 08/100,818, incorporated by reference above, provides for the simplification of the generation of Radon data.

The last three mentioned applications generally provide techniques allowing reconstruction of images using projection data. However, these and other reconstruction techniques may have difficulties in imaging objects and regions which have a rather long, wide, or tall dimension. If the height, width, or length of an object or region is great, it may be impractical or difficult to obtain a detector array with sufficient height or width to obtain projection data from the object or region of interest. Generally, the detector must have a height and width at least somewhat greater than the height and width of the object or region of interest. Otherwise, some x-ray data would be missing. Also, since some x-rays have passed through portions of an object which are not in the region of interest (where the region of interest is only part of an object), the cone beam data collected would not exclusively represent data from such a region of interest.

Some techniques use approximation and other procedures to compensate when the data will be incomplete due to the object or region of interest extending further in one dimension than the detector can image.

U.S. Pat. No. 5,032,990 of Eberhard and Tam, issued Jul. 16, 1991, entitled "TRANSLATE ROTATE SCANNING METHOD FOR X-RAY IMAGING", assigned on its face to the assignee of the present application, and hereby incorporated by reference, discloses a technique for two-dimensional imaging of an object which is so wide that a linear array detector is not wide enough to span the object or part which is to be viewed.

U.S. Pat. No. 5,187,659, in the name of Eberhard and Tam, entitled "CONE BEAM SCANNING TRAJECTORIES FOR THREE-DIMENSIONAL COMPUTERIZED TOMOGRAPHY DATA ACQUISITION WHERE OBJECT IS LARGER THAN THE FIELD OF VIEW", assigned to the assignee of the present application, and hereby incorporated by reference discloses a technique for avoiding corrupted data when performing 3D CT on an object larger than the field of view. (No representation is made or intended that this referenced application is necessarily prior art to the present application.)

U.S. patent application Ser. No. 07/998,330, filed Dec. 30, 1992, in the name of Eberhard, Tam and Hedengren, entitled "THREE DIMENSIONAL COMPUTERIZED TOMOGRAPHY SCANNING CONFIGURATION FOR IMAGING LARGE OBJECTS WITH SMALLER AREA DETECTORS", assigned to the assignee of the present application, and hereby incorporated by reference, discloses the imaging of large-objects using a relatively small detector by moving the detector relative to the source of imaging energy.

Ser. No. 08/131,180, incorporated by reference above, discloses a technique for collecting complete cone beam data of a long or tall object using a short or small detector moved in a helical path.

Although the above and other techniques have been useful, the imaging of a relatively large region of interest portion of an object with a relatively small detector has required processing of data for outside the region of interest and/or scan paths which have abrupt shifts in direction. Since the object being imaged may be a patient, such abrupt shifts in scan direction are undesirable if the patient must be moved for the scanning. Even if the source is moved to obtain an abrupt shift, this is less than desirable.

OBJECTS AND SUMMARY OF THE INVENTION

Accordingly, it is a primary object of the present invention to provide a new and improved 3D tomography system and method.

A more specific object of the present invention is to provide computerized tomography which allows a relatively small detector to image a relatively large object or region of interest, while providing a complete data set of projection data.

Yet another object of the present invention is to provide efficient tomography which minimizes or avoids collection and/or use of unnecessary data.

Yet another object of the present invention is to provide a tomography technique where a manipulator, which causes relative scanning movement of the source and object or region of interest, may use smooth movements (instead of a scan requiring straight segments or other patterns associated with abrupt shifts in direction).

The above and other objects of the present invention which will become more apparent as the description proceeds are realized by a scanning and data acquisition method for three dimensional computerized tomography (CT) imaging of an object partially in a field of view radially centered on a predetermined axis. The method includes applying cone beam energy from a cone beam source to at least a portion of the object, defining a source scanning trajectory as a path traversed by the source, and using the cone beam source fixed relative to an area detector with both source and detector moveably positioned relative to the object to scan about the object. Further, the source scanning trajectory is specified as a first circle, a second circle, and a helical portion connecting the first and second circles and defining a plurality of mutually spaced stages on a predetermined geometric surface surrounding the field of view such that each plane passing through the field of view intersects the scanning trajectory in at least one point. The trajectory satisfies the completeness criteria for the region of interest. The area detector has a predetermined dimension extending sufficiently along a direction generally parallel to the predetermined axis to span at least the two consecutive stages having the largest spacing therebetween. Scanning is performed at a plurality of positions along the source scanning trajectory to obtain cone beam projection data corresponding to respective portions of the object. Cone beam projection data is selected corresponding to energy which is passed only through a region of interest of the object (i.e., not other portions of the object) which is smaller than the object itself and which is completely within the field of view. This provides a data set which can be reconstructed into an image of the region of interest of the object. The field of view is preferably cylindrical. The geometric surface surrounding the field of view is cylindrical and the first and second circles are in parallel planes and have equal diameters. The spacing between any two successive stages along the predetermined axis is substantially equidistant.

The method further includes the step of displaying the region of interest. A Radon process for reconstruction by use only of non-overlapping (i.e., not redundant) cone beam projection data from within the region of interest is performed. The non-overlapping data satisfies the completeness criteria for the region of interest. The cone beam source is used by maintaining the source and detector in stationary positions, while translating and rotating the object so as to effect relative movement of the source with respect to the object. Alternately, the cone beam source is used by maintaining the object in a stationary position while moving the source and detector to achieve relative movement of the source with respect to the object. The predetermined dimension may be the height dimension of the detector in one embodiment. In another embodiment the predetermined dimension is the width dimension of the detector.

Each of a plurality of planes passing through the region of interest is made of portions. The method includes the steps of determining cone beam data for each of the portions of the planes, computing the Radon derivative for each of the portions of the planes, and summing the Radon derivatives for all portions of each of the planes to determine a Radon derivative for each of the planes.

The scanning and data acquisition system for three dimensional computerized tomography imaging of an object in a field of view corresponding to a region of interest radially centered on a predetermined axis according to the present invention includes a cone beam source for applying cone beam energy to at least a portion of the object. A two-dimensional area detector is positioned to receive cone beam energy from the source. A scanning device causes relative motion of the source and object such that the source moves along a scanning trajectory relative to the object. Trajectory defining means are operatively coupled to the scanning device to cause the scanning device to provide a path with a first circle, a second circle and a helical portion having a plurality of mutually spaced stages on a predetermined geometric surface surrounding the field of view such that each plane passing through the field of view intersects the scanning trajectory in at least one point. The area detector has a predetermined dimension extending sufficiently along a direction generally parallel to the predetermined axis to span at least two consecutive stages having the largest spacing therebetween. Means are provided for acquiring cone beam projection data with the source at a plurality of positions along the source scanning trajectory, the cone beam projection data corresponding to respective portions of the object. Means are provided for selecting cone beam projection data corresponding to energy which is passed only through a region of interest of the object (i.e., not through other portions of the object) which is smaller than the object itself and which is completely within the field of view. This provides a data set which can be reconstructed into an image of the object.

The system further includes a display operably connected to the selecting means for displaying an image of the region of interest of the object based upon the generated data set.

The system further includes a means for using a Radon process for reconstruction by use only of data from within the region of interest. Each of a plurality of planes passing through the region of interest is made of portions, Radon derivative data collectively for all of the planes being sufficient to define a complete data set for Radon reconstruction processing. The system includes means for determining cone beam data for each of the portions of the planes, means for computing the Radon derivative for each of the portions of the planes, and means for summing the Radon derivatives for all portions of each of the planes to determine a Radon derivative for each of the planes.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
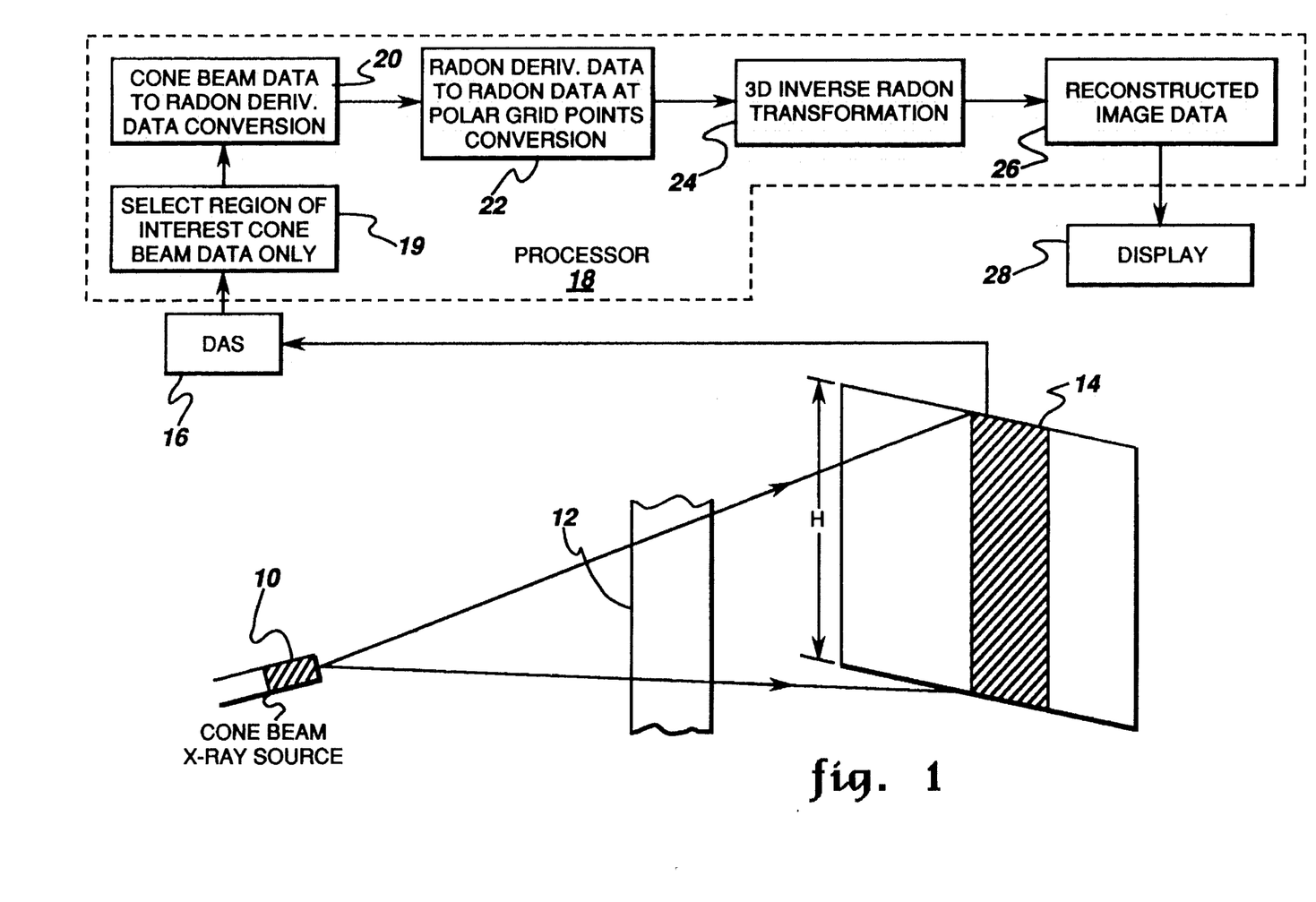
FIG. 1 is a simplified perspective of the imaging of an object using a source and detector and combined with a simplified block diagram of image reconstruction according to the present invention.

As shown in FIG. 1 a cone beam x-ray source 10 generates cone beam energy which passes through and about a region of interest of an object 12 which is to be imaged. Although source 10 is shown as an x-ray source, other types of imaging energy might be used. The imaging energy of whatever type is detected by detector 14. Although individual detector elements are not shown, it will be readily understood that the detector 14 is a two-dimensional array of individual detector elements. Relative movement between the source 10 and object 12 is used to provide complete data about the object 12. For example, the object 12 could be moved in a scan movement as discussed in detail below. Alternately, and equivalently, the source 10 and detector 14 could be moved in such a scan path. The object may be a work piece or a medical patient or other item for imaging.

Signals corresponding to the sensed x-ray energy falling on elements within the detector 14 are supplied to a data acquisition system 16 which, like the previously described portions of FIG. 1, may operate in known fashion.

Cone beam data from the data acquisition system 16 is supplied to a processor 18, which may be a computer programmed to perform various data conversions illustrated by the blocks within the processor 18. Block 19, which is a key feature of the present invention, selects projection or cone beam data corresponding only to the region of interest. As will be discussed in detail below, projection data corresponding to passage through parts of the object other than the region of interest will not be collected and/or will not be used for the Radon data procedure. Next, the selected cone beam data is converted to Radon derivative data at block 20. This may be accomplished using the techniques described in the incorporated by reference U.S. Pat. No. 5,257,183. The Radon derivative data is converted to Radon data at polar grid points at block 22 and using a technique described in detail in the incorporated by reference application Ser. No. 08/100,818. The Radon data at the polar grid points is supplied to block 24 which performs an inverse 3D Radon transformation using the techniques described in detail in the incorporated by reference application Ser. No. 07/631,818.

The processor 18 supplies reconstructed image data at block 26 from the inverse Radon transformation of block 24. The reconstructed data is fed from the processor 18 to a display 28, which may operate in known fashion to provide 3D CT imaging of the object 12 or the region of interest portion (not separately shown in FIG. 1).

The blocks of FIG. 1, other than block 19, are described in more detail in the incorporated by reference applications. Accordingly, the present application will concentrate on the details of block 19 after an explanation of principles used by the present invention.

Figure 2:
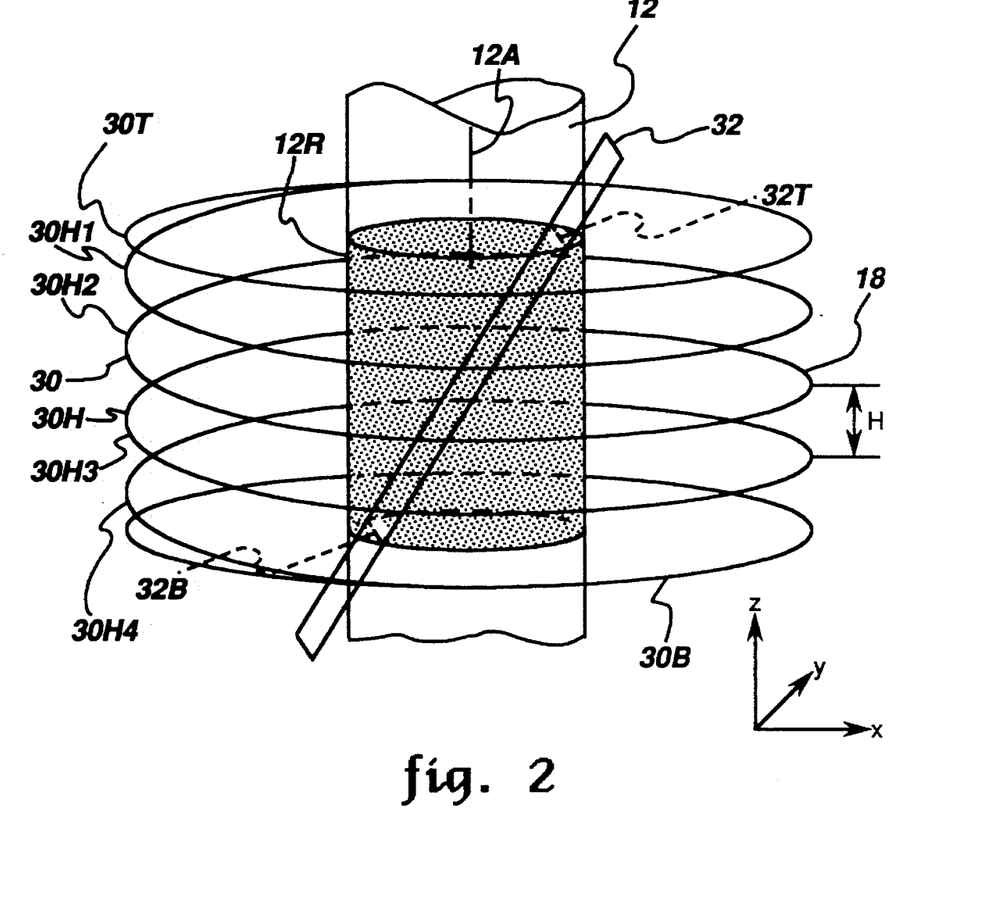
FIG. 2 shows a simplified perspective of a region of interest of an object and a scan path around it.

Turning now to FIG. 2, the object 12 is shown as including a region of interest 12R, which region is less than the total extent of the relatively long or tall object 12. A scan path 30 is illustrated around the region 12R and includes a top circle 30T, a bottom circle 30B, and a helical portion 30H connecting the top circle 30T and the bottom circle 30B. As illustrated, the helical portion 30H has a plurality of stages 30H1, 30H2, 30H3, and 30H4. The stages are mutually spaced by a distance H, which corresponds to the height of detector 14 in FIG. 1. This will allow the detector 14 to assemble a complete set of cone beam or projection data relative to the region 12R without any overlap as explained in more detail in connection with the incorporated by reference application Ser. No. 08/131,180. Top circle 30T, bottom circle 30B, and the various stages of helical portion 30H collectively define a cylinder centered about axis 12A, which is an axis of symmetry of the region of interest 12R. As will be readily understood, the stages of helical portion 30H refer to each of the turns or revolutions formed by the helical path about axis 12A.

The path 30 corresponds to movement of the source 10 (FIG. 1 only) about the object 12, it being understood that the detector 14 (FIG. 1 only) would be maintained in a fixed position relative to the source 10. Instead of scanning the source 10 and detector 14 about the object 12 in the path or trajectory 30 shown in FIG. 2, one could equivalently rotate and move the object 12 to produce the illustrated scan path. In that case, the scan path would illustrate the apparent movement of the source with respect to a frame of reference fixed to the object 12.

In FIG. 1, the object 12 is shown as a relatively long cylinder having a cylindrical region of interest 12R therein. It will be understood that the object may be of other shapes and in that case the region of interest portion of such other object would simply be placed to be within the illustrated region of interest 12R, which later region of interest corresponds to or defines a field of view. The cylinder corresponding to region of interest 12R will be referred to as the object cylinder. That object cylinder is in turn enclosed within a scan path cylinder defined by top circle 30T, bottom circle 30B, and the stages of helical connecting portion 30H which effectively wrap around the imaginary cylindrical surface connecting the two circles.

If a plane 32 is drawn which intersects region of interest 12R, it will intersect the object 12 in an ellipse. Likewise, it will intersect the cylinder corresponding to the path 30 in an ellipse.

Figure 3:
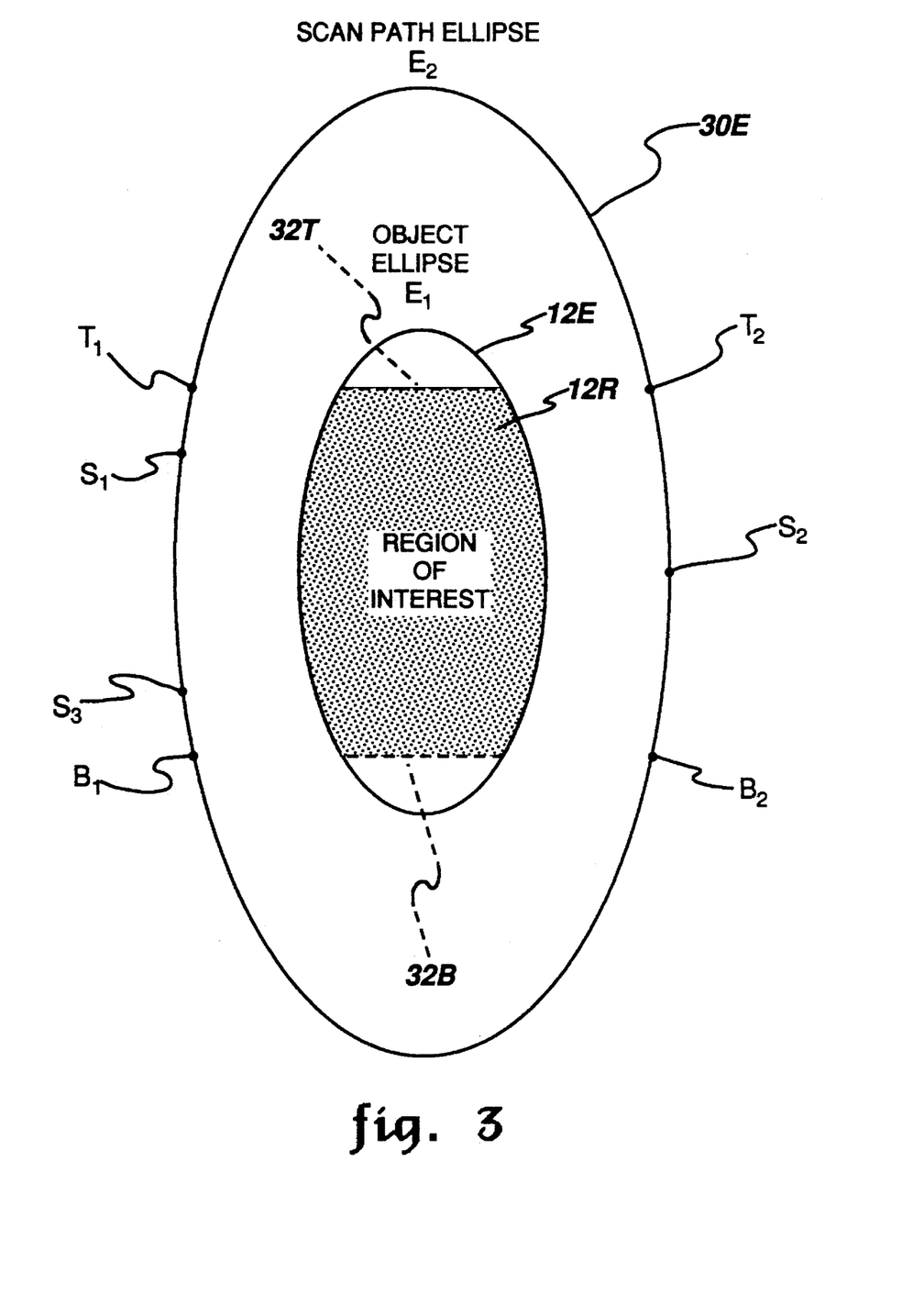
FIG. 3 shows a view taken in a plane 32 of FIG. 2.

Turning now to FIG. 3, this is the view of the object 12 and scan path 30 of FIG. 2 when taken in plane 32 of FIG. 2. The intersection between the plane 32 and scan path 30 defines the ellipse 30E, whereas the intersection between the plane 32 and the object 12 defines an object ellipse 12E. For the particular plane 32 of FIG. 2 (referring back momentarily to FIG. 2), the region of interest 12R is only that portion of ellipse 12E (FIG. 3) which is between 32T and 32B corresponding to the intersection of plane 32 in FIG. 2 with the top and bottom of the region of interest 12R.

Since the helical portion 30H lies on the scan path cylinder corresponding to path 30, the intersections between the helical portion 30H and the plane are points that lie on the ellipse 30E. These source positions are labeled $S_1$, $S_2$, and $S_3$ in FIG. 3. For ease of illustration and discussion, it is assumed that there are only three such points, but it will be readily understood that normally a large number of points of intersection would occur and would be utilized. It should be appreciated that the top circle 30T of FIG. 2 intersects the plane 32 of FIG. 2 in two points $T_1$ and $T_2$ which lie at the intersection between 30E and the top edge of the region of interest 12R. Likewise, the bottom circle 30B of FIG. 2 intersects the plane 32 in the two points $B_1$ and $B_2$ which lie at the intersection between ellipse 30E and the bottom edge of region of interest 12R.

In order to image the region of interest 12R, one needs the Radon derivative for the portion of plane 32 that lies within the region of interest. Whereas previous techniques generally would obtain a Radon derivative for a plane including contributions from portions outside the region of interest, the present invention allows one to efficiently obtain the Radon derivative data only for the portion of the plane within the region of interest such that less data need be processed and contributions from portions outside the region of interest need not be subtracted out at a later stage in the data processing.

Figure 4:
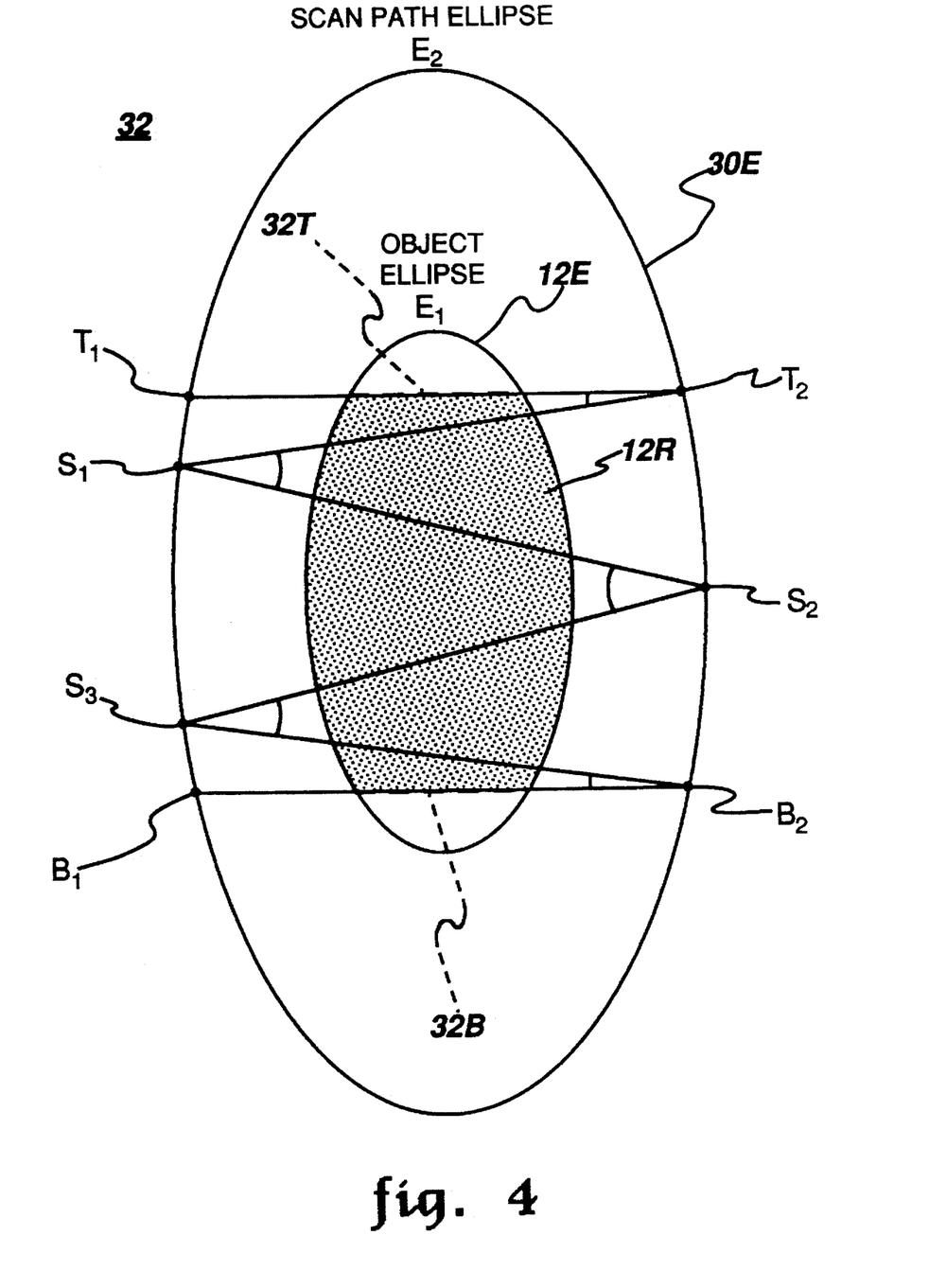
FIG. 4 shows the same view as FIG. 3 with an indication of which cone beam data is used.

With reference now to FIG. 4, it is illustrated how the present invention selects non-overlapping cone beam data corresponding to beams which pass only through the region of interest part of the object 12. FIG. 4 is similar to FIG. 3 except with lines drawn to indicate beams of x-rays or other imaging energy. The Radon derivative for the region of interest 12R corresponding to the plane 32 of FIG. 2 may be considered to be the sum of partial results computed from the cone beam data at the various source positions on the ellipse 30E. When the source is at position $T_2$ the detector (not shown in FIG. 4) would be detecting energy relative to the plane of view of FIG. 4 corresponding to rays of energy between lines T1 T2, and S1 T2. That projection data would provide the cone beam data corresponding to the segment of 12R in FIG. 1 which is between the indicated lines and over the angle $T_1\ T_2\ S_1$.

When the source is at position $S_1$ in FIG. 4, cone beam data corresponding to angle $T_2\ S_1\ S_2$ will be collected and utilized. This partial result will be the cone beam or projection data corresponding to that portion of 12R between lines $S_1\ T_2$ and $S_1\ S_2$.

In similar fashion, when the source is at position $S_2$, the detector (not shown in FIG. 4) will collect data corresponding to that portion of 12R between lines $S_1\ S_2$ and $S_2\ S_3$.

When the source is at position $S_3$, cone beam data will be gathered corresponding to the angle $S_2\ S_3\ B_2$. As with the other source positions, it will be appreciated that the detector, not shown in FIG. 4, would be disposed at the curve $S_2\ B_2$ in order to capture the energy supplied from source position $S_3$. In other words, and as always is the case, the detector would be opposite the source position.

Finally, when the source position is at $B_2$, the projection data would be collected and utilized corresponding to that portion of region of interest 12R between lines $S_3 B_2$ and $B_2 B_1$.

By obtaining the five partial results corresponding to the five source positions $T_2$, $S_1$, $S_2$, $S_3$ and $B_2$, one can readily determine the Radon derivative for all of the illustrated plane corresponding to that portion of region of interest 12R in the plane of view of FIG. 4. Basically, one can simply find Radon derivatives for the five partial results corresponding to the five source positions and associated angles illustrated in FIG. 4. The five Radon derivatives may then be added to obtain the Radon derivative for the plane of the region of interest. It will be appreciated that the lines $T_1 T_2$ and $B_1 B_2$ correspond respectively to lines 32T and 32B such that this summation of the partial results will provide a Radon derivative for the entire portion of the plane 32 which is within the region of interest 12R. With reference momentarily back to FIG. 2, it will be appreciated that this technique avoids having to compute Radon derivative data for portions of the object 12 which are outside the region of interest 12R.

As discussed previously, the source positions corresponding to the helical portion 30H of FIG. 2 would likely be more numerous than the three source positions $S_1$, $S_2$ and $S_3$ used for illustrative purposes herein.

With reference back to FIG. 2, it will be appreciated that the ellipses 30E and 12E of FIG. 4 will both be circles when the plane 32 is parallel to the xy plane of FIG. 2. However, the calculations may be performed in the same fashion. Likewise, if the plane 32 of FIG. 2 is parallel to the axis 12A, the calculations may be performed in the same fashion as discussed notwithstanding the fact that the plane 32 would intersect the region of interest in such a way as to define a rectangle at the intersection.

Figure 5:
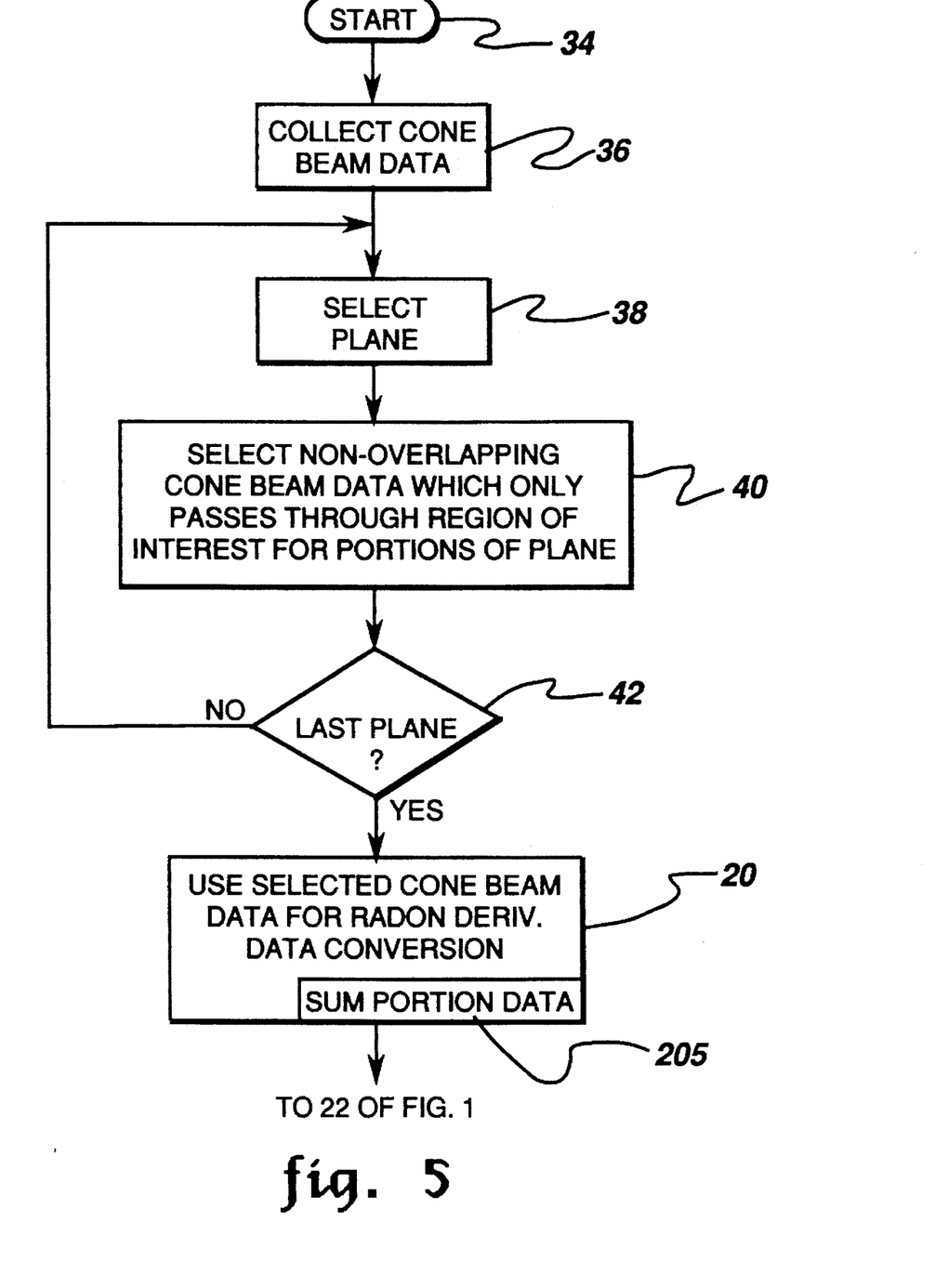
FIG. 5 shows a simplified flowchart of data selection according to the present invention.

With reference now to FIG. 5, a simplified flowchart illustrates a manner in which the present invention may proceed. The start block 34 leads to block 36 whereat cone beam data is collected. The cone beam data would be collected while the source and detector were scanned in the pattern of scan 30 of FIG. 2. As discussed previously, the scanning of the source and detector may be accomplished by moving the source and detector together, while keeping the object 12 stationary, or, alternately, by moving the object 12, while keeping the source and detector stationary.

After block 36 has collected the cone beam data, control transfers to block 38 which selects a particular plane 32 for which cone beam data is desired. For example, block 38 might initially select a plane 32 parallel to the xy plane of FIG. 2. Block 38 transfers control to block 40 which selects non-overlapping cone beam data corresponding to rays of energy which have passed only through the region of interest. This utilizes the technique explained in detail with respect to FIG. 4. Basically, block 40 computes the cone beam data for the different portions of the plane corresponding to the different source positions and angles as discussed with respect to FIG. 4.

Next, control transfers to block 42 which tests to determine if the last plane has been covered. If not, control transfers back to box 38 which selects a new plane, this loop being continued until all planes passing through the region of interest have been selected. Selecting all planes requires iterations relative to two angles (orientation) and positioning of the plane. In other words, and assuming that the initial plane was parallel to the xy plane, the second plane might be rotated about the y axis (refer to FIG. 2) by one degree. Subsequent planes would be rotated about the y axis by one degree. In order to cover all of the planes, one would also require rotation about the x axis and this may be done using known techniques. Selecting all planes would require three nested loops corresponding to r, θ and φ, where r is the distance between the origin and the closest point on the plane, and θ and φ denote the polar and azimuthal angles respectively of the normal to the plane. In other words, the loop between block 38 and block 42 would select all planes having an angular and position spacing as established or required.

Following the selection of cone beam data from the last plane, block 42 would transfer control to block 20 which would use the selected cone beam data to compute Radon derivative data using the techniques of the incorporated by reference applications. In particular, block 20 may compute the Radon derivative for each of the five segments of the intersection between the region of interest 12R and the plane of view of FIG. 4. Having computed the Radon derivative separately for each of these five portions in FIG. 4 for example, the Radon derivatives could be added together (as indicated at part 205 of block 20) in order to obtain the overall Radon derivative for the union of the five segments corresponding to the intersection of region of interest 12R with the plane of view of FIG. 4.

Figure 6:
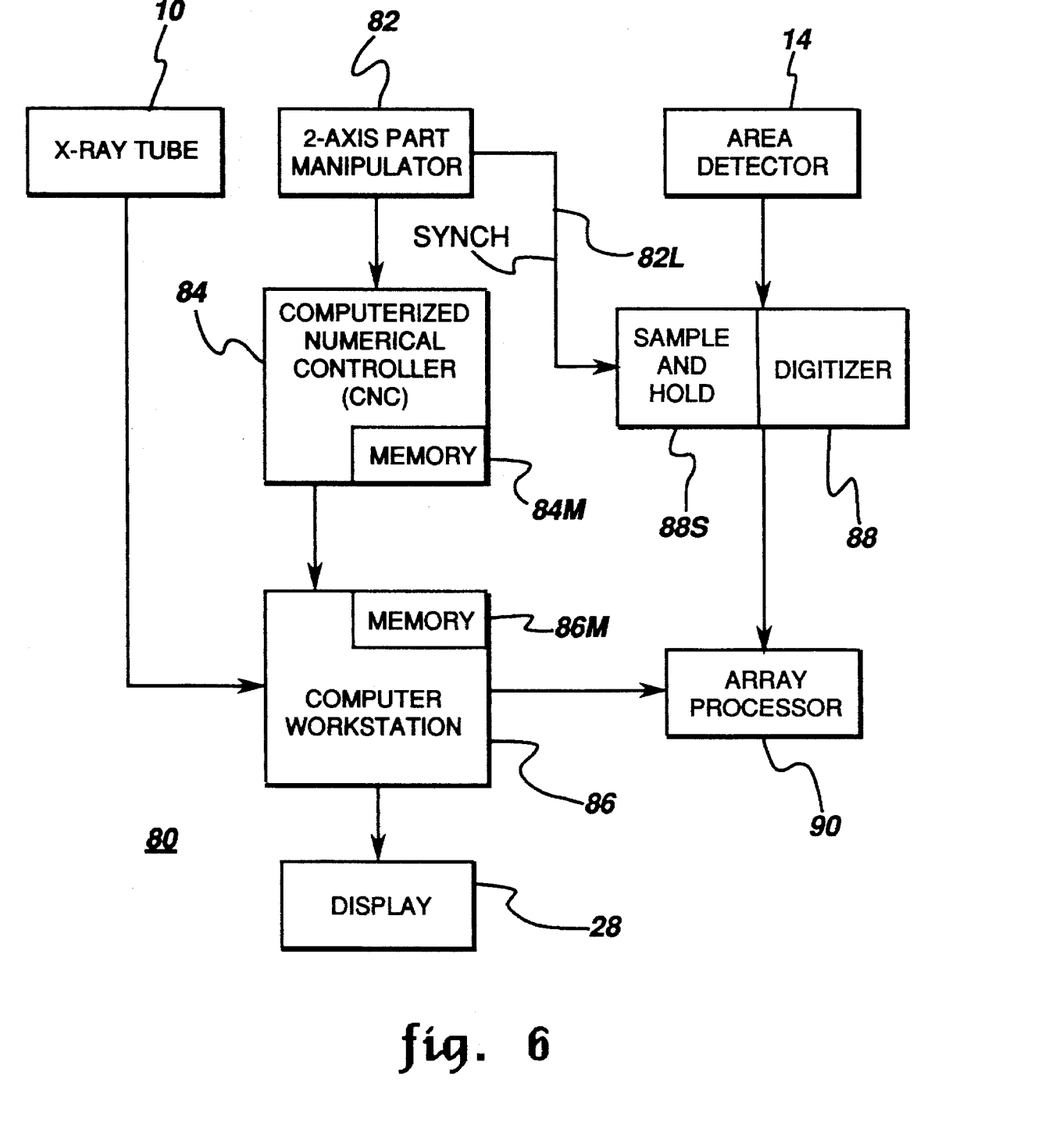
FIG. 6 shows a simplified block diagram of the present invention.

Turning now to FIG. 6, a system 80 according to the present invention will be discussed. The system includes the source 10 and area detector 14. Although the source 10 has been shown as an x-ray tube, the cone beam source 10 could alternately provide neutrons, positrons, or other forms of radiation or electron magnetic energy from a point source. Alternately, other forms of imaging energy might be used.

A manipulator 82, which may be a two-axis part manipulator, is used to provide the relative scanning movement between the object (not shown in FIG. 6) which is used to be imaged and the source 10. Although the manipulator 82 is designed to move the object, the manipulator 82 might alternately move the source 10.

The manipulator 82 is controlled by a known computerized numerical controller 84, which may, for example, be of a type made by Aerotech. The controller 84 may include a memory 84M having data defining various scan paths in known fashion. Alternately, and also using well known techniques, a memory 86M of a computer work station 86, which is connected to the controller 84, may have the data which defines movements of the manipulator 82 and therefore defines the scan path or trajectory. In either case, the defined scan paths would be the two parallel circles with helical turns interconnecting them as discussed in detail above. The computer work station 86 (which may include the processor 18 of FIG. 1) may be a work station made by Sun, although other computer work stations and possibly even personal computers might be used in place of the work station. The computer work station controls the other components of the system 80 in known fashion.

Connected to the area detector 14 is a digitizer 88 which operates in known fashion to convert analog signals from the area detector into digital signals representative of the image of the object under test. The digitizer 88 may include sample and hold circuits 88S operating in response to a synch signal on line 82L in known fashion.

The digitized values corresponding to the sense radiation from the detector elements within detector 14 are supplied by the digitizer 88 to a data array processor 90. The array processor 90, which may be of a known commercially available type such as a Meiko M40, provides the necessary signal processing for the signals coming from the digitizer 88. the array processor 90 (which may include or be the processor 18 of FIG. 1) may perform the necessary image reconstruction and processing such that a display might be connected directly to the array processor to display the images from the CT scan. However, in the arrangement shown in FIG. 6, the image data from array processor 90 is supplied to computer work station 86 and the computer work station 86 in turn supplies the data, with or without further processing, to the display 28 which displays the CT images. The computer 86 or, more preferably, array processor 90 reconstructs an image from the projection data.

Although specific constructions and steps have been described herein, it is to be understood that these details are for illustrative purposes only. Various modifications and adaptations will be apparent to those of skill in this art. Accordingly, the scope of the present invention should be determined by reference to the claims appended hereto.

What is claimed is:

1. A a scanning and data acquisition method for three-dimensional computerized tomography (CT) imaging of an object only partially in a field of view radially centered on a predetermined axis, the method comprising the steps of:

applying cone beam energy from a cone beam source to at least a portion of the object;

defining a source scanning trajectory as a path traversed by the source;

using the cone beam source fixed relative to an area detector with both source and detector moveably positioned relative to the object to scan about the object;

specifying the source scanning trajectory as a first circle, a second circle, and a helical portion connecting the first and second circles and defining a plurality of mutually spaced stages on a predetermined geometric surface surrounding the field of view such that each plane passing through the field of view intersects the scanning trajectory in at least one point, the area detector having a predetermined dimension extending sufficiently along a direction generally parallel to the predetermined axis to span at least the two consecutive stages having the largest spacing therebetween;

scanning at a plurality of positions along the source scanning trajectory to obtain cone beam projection data corresponding to respective portions of the object; and selecting cone beam projection data corresponding to energy which is passed only through a region of interest of the object which is smaller than the object itself and which is completely within the field of view to provide a data set which can be reconstructed into an image of the region of interest of the object.

2. A method in accordance with claim 1 wherein the field of view is cylindrical.

3. A method in accordance with claim 2 wherein the geometric surface surrounding the field of view is cylindrical and the first and second circles are in parallel planes and have equal diameters.

4. A method in accordance with claim 3 wherein the spacing between any two successive stages along the predetermined axis is substantially equidistant.

5. A method in accordance with claim 1 further comprising displaying the region of interest.

6. A method in accordance with claim 1 further comprising using a Radon process for reconstruction by use only of non-overlapping data from within the field of view, said non-overlapping data satisfying completeness criteria for the region of interest.

7. A method in accordance with claim 1 wherein the step of using the cone beam source comprises maintaining the source and detector in stationary positions while translating and rotating the object so as to effect relative movement of the source with respect to the object.

8. A method in accordance with claim 1 wherein the step of using the cone beam source comprises maintaining the object in a stationary position while moving the source and detector to achieve relative movement of the source with respect to the object.

9. A method in accordance with claim 1 wherein the predetermined dimension is the height dimension of the detector.

10. A method in accordance with claim 1 wherein the predetermined dimension is the width dimension of the detector.

11. A method in accordance with claim 1 wherein each of a plurality of planes passing through the region of interest is made of non-overlapping portions and further comprising determining cone beam data for each of the portions of the planes, computing the Radon derivative for each of the portions of the planes, and summing the Radon derivatives for all portions of each of the planes to determine a Radon derivative for each of the planes.

12. A scanning and data acquisition method for three-dimensional computerized tomography (CT) imaging of an object only partially in a field of view corresponding to a region of interest radially centered on a predetermined axis, the system comprising:

a cone beam source for applying cone beam energy to at least a portion of the object;

a two-dimensional area detector is positioned to receive cone beam energy from the source;

a scanning device causes relative motion of the source and object such that the source moves along a scanning trajectory relative to the object;

trajectory defining means are operatively coupled to the scanning device to cause the scanning device to provide a path with a first circle, a second circle and a helical portion having a plurality of mutually spaced stages on a predetermined geometric surface surrounding the field of view such that each plane passing through the field of view intersects the scanning trajectory in at least one point. the area detector having a predetermined dimension extending sufficiently along a direction generally parallel to the predetermined axis to span at least two consecutive stages having the largest spacing therebetween;

means for acquiring cone beam projection data with the source at a plurality of positions along the source scanning trajectory, the cone beam projection data corresponding to respective portions of the object; and means for selecting cone beam projection data corresponding to energy which is passed only through a region of interest of the object which is smaller than the object itself and which is completely within the field of view to provide a data set which can be reconstructed into an image of the region of interest of the object.

13. The system in accordance with claim 12 further comprising a display operably connected to the selecting means for displaying an image of the region of interest of the object based upon the generated data set.

14. The system in accordance with claim 13 wherein the geometric surface surrounding the field of view is cylindrical and the first and second circles are in parallel planes and have equal diameters.

15. The system in accordance with claim 14 wherein the spacing between any two successive stages along the predetermined axis is substantially equidistant.

16. The system in accordance with claim 12 wherein the scanning device comprises a two-axis CNC part manipulator connected to the object for translating and rotating the object so as to effect relative movement of the source with respect to the object while the source and detector remain stationary.

17. The system in accordance with claim 12 wherein the scanning device comprises a two-axis CNC part manipulator connected to the source and detector to achieve relative movement of the source with respect to the object while the object remains stationary.

18. The system in accordance with claim 12 wherein the predetermined dimension is the height dimension of the detector.

19. The system in accordance with claim 12 wherein the predetermined dimension is the width dimension of the detector.

20. The system in accordance with claim 12 further comprising means using a Radon process for reconstruction by use only of non-overlapping data from within the field of view, said non-overlapping data satisfying completeness criteria for the region of interest.

21. The system in accordance with claim 12 wherein each of a plurality of planes passing through the region of interest is made of non-overlapping portions and further comprising means for determining cone beam data for each of the portions of the planes, means for computing the Radon derivative for each of the portions of the planes, and means for summing the Radon derivatives for all portions of each of the planes to determine a Radon derivative for each of the planes.

* * * * *